US00PP31990P2

(12) United States Plant Patent
Brown et al.

(10) Patent No.: US PP31,990 P2
(45) Date of Patent: Jul. 21, 2020

(54) ***CHERIMOYA* TREE 'RINCON'**

(50) Latin Name: Annona cherimola
Varietal Denomination: Rincon

(71) Applicants: Anthony Edwin Brown, Carpinteria, CA (US); Christine Beatrice Brown, Carpinteria, CA (US); Jehanne Khoury Brown, Carpinteria, CA (US)

(72) Inventors: Anthony Edwin Brown, Carpinteria, CA (US); Christine Beatrice Brown, Carpinteria, CA (US); Jehanne Khoury Brown, Carpinteria, CA (US)

( * ) Notice: Subject to any disclaimer, the term of this patent is extended or adjusted under 35 U.S.C. 154(b) by 0 days.

(21) Appl. No.: 16/350,741

(22) Filed: Dec. 28, 2018

(51) Int. Cl.
*A01H 5/00* (2018.01)

(52) U.S. Cl.
USPC ..... Plt./156

(58) Field of Classification Search
USPC ..... Plt./156
CPC ..... A01H 5/00
See application file for complete search history.

*Primary Examiner* — Annette H Para

(57) ABSTRACT

The new and distinct variety of *cherimoya* tree, "Annona Cherimola," is of large size, vigorous, spreading growth, and a regular and productive bearer of large-sized fruits with firm white flesh with excellent mango-like flavor and eating quality with flesh that is smooth in texture. Seeds are smaller than average for the species. Stem is smaller than average for the species, lending to a more favorable fruit ratio. In comparison with conventional commercial *cherimoyas* grown under the same conditions, the new variety has flesh remaining in firm condition longer under storage, with superior texture, and high soluble solids (average 23.0 Brix).

2 Drawing Sheets

Species of the plant claimed: "Annona Cherimola."
Variety denomination: New.

BACKGROUND

A new and improved variety of *cherimoya* tree "Annona Cherimola" which has the following unique combination of desirable features that are outstanding in a new variety:

1. Regular and productive bearer under usual artificial pollination.
2. Fruits are of excellent flavor and high soluble solids (average Brix 23.0).
3. Flesh is outstandingly firm, of mango-like density, withstanding market handling.
4. Fruits rarely split when maturing to a marketable stage, regardless of temperature or soil moisture.
5. Tree of remarkable hardiness.

ORIGIN OF THE VARIETY

The new and distinct variety of *cherimoya* tree was originated by the inventors in their orchard located near Carpinteria, Calif., as a seedling derived from an open-pollinated cross of 'McPherson' *cherimoya*. The present variety exhibited the distinctive desirable fruit characteristics described above and was selected for asexual reproduction and commercialization after many years of observation.

The Subtropical Fruit Crops Department at the university in Malaga, Spain completed a cultivar ID, or fingerprinting, for this Rincon variety. They used 9 loci of microsatellite markers (those that are routinely used for *cherimoya* fingerprinting) and the results show that the Rincon material is different from all the over 300 accessions they have in their collection, therefore parents are unknown.

See FIG. 1 for the alleles that were obtained for the 9 loci. SSR, labeled in FIG. 1 means Simple Sequence Repeat and refers to particular parts of the DNA that are useful to distinguish *cherimoya* accessions. In this case, each SSR is one region of the DNA. So, LMCH1 will be a region different from LMCH4 and so on. Then for each region, each *cherimoya* accession will have two fragments (one for each of the two copies of the chromosome, called alleles). The combination of all the alleles for all the SSRs provides a unique fingerprint for the accession. Once that information is obtained, results are compared with all the accessions in their database. The Rincon accession is closely related, for example, to some other California varieties, such as White or McPherson, however, even with it being closely related, is different for some of the alleles from all of them.

ASEXUAL REPRODUCTION OF THE VARIETY

The present new *cherimoya* variety was asexually propagated by the inventors during 2008 in our experimental orchard located near Carpinteria, Calif., by grafting, and the asexually propagated trees show that said characteristics of the original tree and its fruits are established and transmitted through succeeding propagations.

SUMMARY OF THE VARIETY

The new and distinct variety of *cherimoya* tree is of large size, vigorous, spreading growth, and a regular and productive bearer of large-sized fruits with firm white flesh with excellent flavor and eating quality. In comparison with conventional commercial *cherimoyas* grown under the same conditions, the new variety has flesh remaining in firm condition longer under storage, with superior texture, and high soluble solids (average 23.0 Brix). Whereas other current commercial varieties, such as White, Bays, and Lisa might show signs of bronze coloration on the skin of the fruit, this new variety shows no signs of bronze coloration on the tree and has a richer, distinctive flavor and texture. The Lisa variety, it should be noted, was purposely cross-pollinated between McPherson and Bays for development in 1971 by the same Anthony Brown in Carpinteria, Calif. Most notable in this new Rincon variety is the distinctive appearance of the fruit, as demonstrated in the accompanying illustration, as well as the flavor, that is reminiscent of a creamy mango.

PHOTOGRAPHS OF THE VARIETY

The accompanying color illustration by photographic reproduction, are of typical specimens of foliage and fruit of the new and distinct *cherimoya* tree. The upper and partial lower surface of the leaves are shown. The exterior and longitudinal section views of the fruit are shown to expose flesh and core coloration with seeds remaining in place. The illustrations were made shortly after collection of the specimens from the tree, the fruit at commercial maturity (firm ripe) and colors are as nearly true as reasonably possible in a color representation of this type.

DESCRIPTION OF THE VARIETY

The following is a botanically detailed description of the new and distinct variety of *cherimoya* tree, "Annona Cherimola," based upon observations of specimens grown at Carpinteria, Calif.

All color code designations are by reference to *The R.H.S. Colour Chart* (1966) of The Royal Horticultural Society, which utilizes Color Group numbers only and avoids use of vernacular color names. All vernacular names for colors not followed by the word "Group" are therefore intended in their common speech meaning only.

Tree:

*Size, relative*.—Medium.
*Vigor*.—Robust.
*Form*.—Spreading.
*Density*.—Dense, branching well.
*Production*.—Regular under artificial pollination.
*Disease resistance*.—Typical for the species.
*Drought tolerance*.—Above average for the species.
*Age*.—Approximately twenty (20) years old.
*Soil type*.—Sandy loam.
*Growing conditions*.—Coastal Mediterranean climate of Southern California.

Trunk:

*Size, relative*.—Medium. Multiple trunks (5) from ground level, ranging in size from 4"-6" in diameter.
*Texture*.—Smooth, not cracking into fissures, leaving rather smooth surface. With age, trunk can exhibit some cracking.
*Color*.—Greyed-Orange Group 177A, reticulated with Greyed-Orange Group 164B.
*Lenticels*.—Few or none, indistinct with age.

Branches:

*Size, relative*.—Small to medium, to 50 mm. diameter at five years of age; leafy portion of annual flush to 1.2 m. in length.
*Texture*.—Smooth, obscurely reticulated in first year.
*Color*.—Greyed-Orange Group 176B.
*Lenticel length*.—5 mm.
*Lenticel width*.—5 mm.
*Shoot color*.—As for matured branch, Greyed-Orange Group 176B.

Leaves:

*Size, relative*.—Uniformly large along branch, excepting terminal 2-3 leaves, which are reduced.
*Form*.—Blade broad elliptical, slightly reflexed; invariably asymmetrical, the halves being of unequal width; apex obtuse.
*Ratio*.—Length:Breadth=1.5.
*Width*.—90 mm.
*Length*.—140 mm, excluding petiole.
*Texture, upper*.—Tomentose.
*Texture, lower*.—Glabrous.
*Color, upper*.—Green Group 137A.
*Color, lower*.—Yellow-Green Group 146B.
*Venation*.—Lateral ribs nearly parallel; veins slightly raised above, strongly raised below.
*Margin*.—Entire.
*Thickness*.—Average for the species.
*Petiole length*.—Short, 12 mm.
*Petiole color*.—Yellow-Green Group 147A.

Flowers:

*Abundance*.—At every node for basal two-thirds of branch.
*Self-fertility*.—Self-compatible.
*Bloom date*.—25 Mar. 2018 through 15 Sep. 2018 at Carpinteria, Calif.
*Bud pubescence*.—Completely covered.
*Size, relative*.—Large.
*Bud form*.—Broad-conic.
*Buds per node*.—1.
*Flower diameter*.—22 mm.
*Petal size, rel*.—Average for species.
*Exterior petal color*.—Greyed-Green Group 194C.
*Interior petal color*.—Green-White Group 157C.
*Petal length*.—32 mm.
*Petal width*.—5 mm.
*Pedicel color*.—Greyed-Green Group 194C.
*Pedicel thickness*.—4 mm.
*Pedicel length*.—20 mm.
*Stamen*.—Not exerted.
*Pollen production*.—Fair.
*Pollen color*.—White Group 158B (fresh).

Fruits:

*Maturity*.—As described, ripe for harvest and shipment approximately 24 December through 7 May 2018 under conditions generally prevailing at Carpinteria, Calif.
*Use*.—Dessert; Eaten fresh.
*Quality*.—Storage, excellent; Transport, excellent.
*Size*.—Large, 400-600 gm. average weight.
*Axial diameter*.—14 cm average.
*Transverse diameter*.—11 cm average.
*Form*.—Elliptic.
*Base*.—Retuse.
*Stem cavity length*.—Deep.
*Stem cavity color*.—Scar tissue along line of dehiscence Orange-Brown Group 113B; Cavity interior Orange-Red 96C.
*Surface*.—Imbricate; Carpels of basal third expressed on skin as distinct, mammillate processes; Carpels of mid-fruit expressed as raised lumps; Carpels of apical third expressed as flat, shield-shaped scales, with a raised medial line for half length of scale.
*Skin thickness*.—Medium, tenacious to flesh.
*Skin texture*.—Finely downy-pubescent.
*Skin color*.—Yellow-Green Group 151A; edges of carpels Yellow-Green Group 148B.

Flesh:

*Texture*.—Firm, rendering juice freely.

*Aroma*.—Intermediate.

*Flavor*.—Distinct, mango-like.

*Soluble solids*.—23.0 deg. Brix at 7 pounds pressure firmness.

*Color*.—Greyed-Yellow Group 162D.

Seeds:

*Type*.—Free within aril, attached by fiber from central core.

*Shape*.—Slightly curved.

*Length*.—25 mm.

*Width*.—12 mm.

*Base*.—Laterally compressed, a single pit at point of fiber insertion.

*Apex*.—Pointed, acute.

*Sides*.—Unequal, slightly curved.

*Color*.—Brown Group 200A.

It should be noted that the tree, flowers, and fruit may vary in slight details due to variations in soil type, cultural practices and climatic conditions.

The invention claimed is:

1. A new and distinct variety of *cherimoya* tree substantially as illustrated, described, and scientifically determined in a lab with genetic fingerprinting, characterized by its moderate size, broad growth and regular bearer of middle season, large sized, remarkably firm fleshed fruits with excellent mango like flesh flavor and transport resistance.

* * * * *

FIG. 1

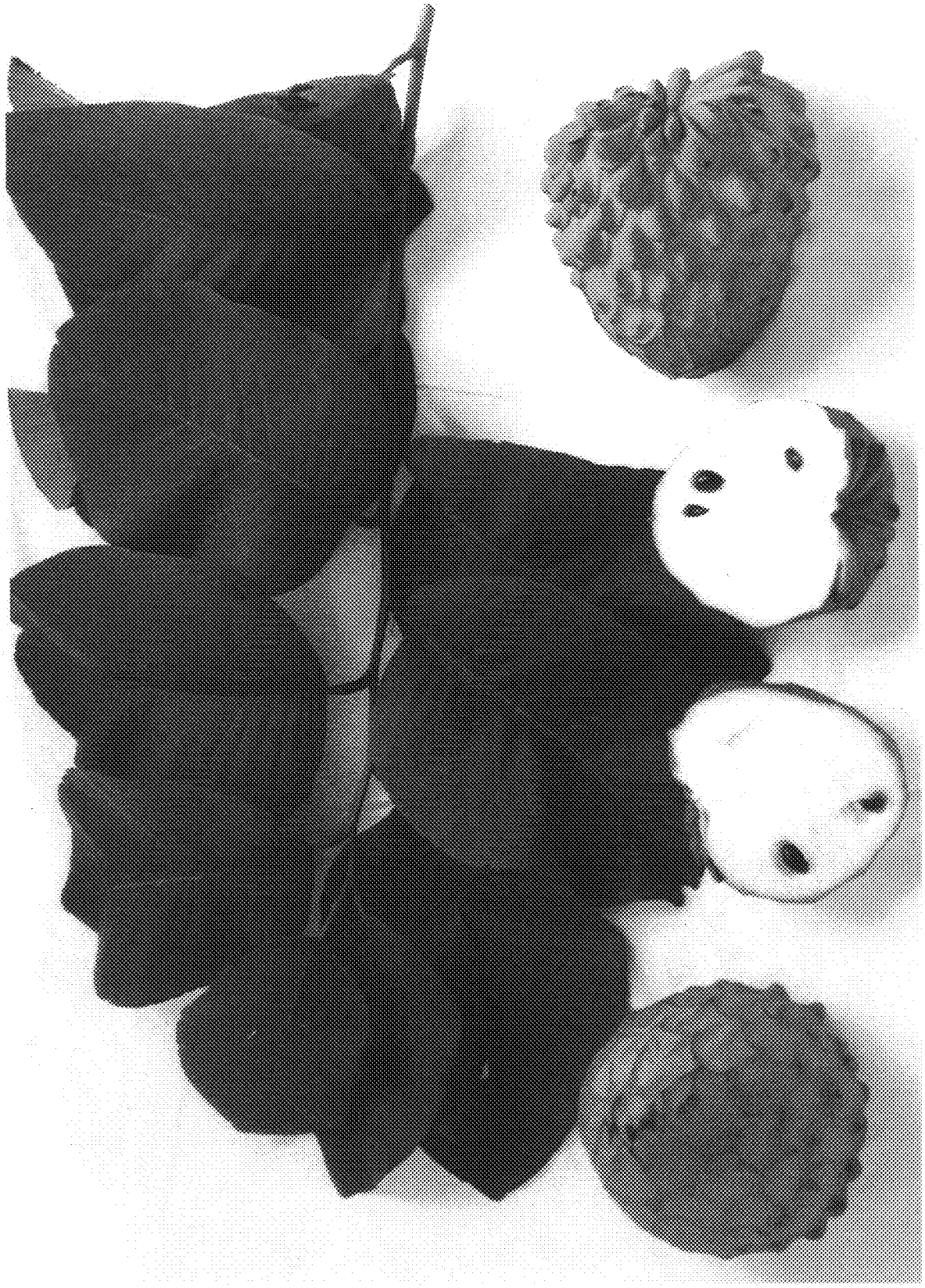

| | A | B |
|---|---|---|
| 1 | | |
| 2 | SSRs | Amplification fragments |
| 3 | LMCH 1 | 291-293 |
| 4 | LMCH 4 | 122-122 |
| 5 | LMCH 16 | 216-230 |
| 6 | LMCH 48 | 141-147 |
| 7 | LMCH 69 | 156-164 |
| 8 | LMCH 87 | 142-148 |
| 9 | LMCH 122 | 183-207 |
| 10 | LMCH 139 | 311-315 |
| 11 | LMCH 144 | 195-197 |